US006484105B2

(12) United States Patent
Zhang

(10) Patent No.: US 6,484,105 B2
(45) Date of Patent: *Nov. 19, 2002

(54) METHOD FOR OBTAINING A PLANT WITH A GENETIC LESION IN A GENE SEQUENCE

(75) Inventor: Yuelin Zhang, Davis, CA (US)

(73) Assignee: Maxyag, Inc., Redwood City, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/285,512

(22) Filed: Apr. 2, 1999

(65) Prior Publication Data

US 2002/0064879 A1 May 30, 2002

Related U.S. Application Data

(60) Provisional application No. 60/080,401, filed on Apr. 2, 1998.

(51) Int. Cl.$^7$ .......................... G06F 19/00; C12Q 1/68; C07H 21/04
(52) U.S. Cl. ............................ 702/20; 435/6; 536/23.1
(58) Field of Search .................... 435/6, 91.2; 536/23.1; 702/20

(56) References Cited

U.S. PATENT DOCUMENTS

| | | | | |
|---|---|---|---|---|
| 5,223,605 A | * | 6/1993 | Fanslow et al. | ............. 530/350 |
| 5,733,732 A | * | 3/1998 | Campbell et al. | ............... 435/6 |
| 5,777,888 A | * | 7/1998 | Rine et al. | ................... 364/496 |
| 5,801,233 A | * | 9/1998 | Haselkorn et al. | .......... 536/23.6 |
| 5,859,351 A | * | 1/1999 | Staskawicz et al. | ........ 800/301 |
| 5,863,731 A | * | 1/1999 | Romaine et al. | ................ 435/6 |
| 5,953,727 A | | 9/1999 | Maslyn et al. | |
| 5,994,075 A | | 11/1999 | Goodfellow | |
| 6,090,586 A | * | 7/2000 | Bergstrom et al. | .......... 435/69.3 |
| 6,107,544 A | * | 8/2000 | Ryals et al. | .................. 800/265 |
| 6,114,114 A | * | 9/2000 | Seilhamer et al. | ............. 435/6 |

OTHER PUBLICATIONS

Ferlin et al. Detection of mitochondrial DNA deletions by a screening procedure using the polymerase chain reaction 174:221–225 1997.*

McKinney, et al. "Sequence–based identification of T–DNA insertion mutations in Arabidopsis: actin mutants act2–1 and act4–1"; *The Plant Journal* 8(4), 613–622 (1995).

Zwaal, et al. "Target–selected gene inactivation in *Caenorhabditis elegans* by using a frozen transposon insertion mutant bank"; *Proc. Natl. Acad. Sci, USA*, vol. 90, pp. 7431–7435 Aug. 1993.

Jansen, et al., "Reverse genetics by chemical mutagenesis in *Caenorhabditis elegans*"; *Nature Genetics*, vol. 17, pp 119–121, Sep. 1997.

Krysan, et al., "Identification of transferred DNA insertions within Arabidopsis genes involved in signal transduction and ion transport"; *Proc. Natl. Acad. Sci. USA*, vol. 93, pp. 8145–8150, Jul. 1996.

Das, et al., Site–Selected Transposon Mutagenesis at the hcf106 Locus in Maize; *The Plant Cell*, vol. 7, pp. 287–294, Mar. 1995.

Fritz, et al., "Identification of Selected Gamma–Ray Induced Deficiencies in Zebrafish Using Multiplex Polymerase Chain Reaction"; *Genetics* 144: 1735–1745, Dec. 1996.

Haig H. Kazazian, Jr., "Use of PCR in the Diagnosis of Monogenic Disease"; PCR Technology: Principles and Applications for DNA Amplification , pp 153–169 (1989)—Publisher: Stockton Press, New York.

Okubara, et al., "Mutants of Downy Mildew Resistance in *Lactuca sativa* (Lettuce)"; *Genetics* 137: 867–874 Jul., 1994.

Nambara, et al., "Isolation of an Internal Deletion Mutant of the *Arabidopsis thaliana* ABI3 Gene"; *Plant Cell Physiol.*, 35(3):509–513 (1994).

Shirley, et al., "Effects of Ionizing Radiation on a Plant Genome: Analysis of Two Arabidopsis transparent testa Mutations"; *The Plant Cell*, vol. 4, 333–347, Mar. 1992.

Bensen, et al., "Cloning and Characterization of the Maize An1 Gene"; *The Plant Cell*, vol. 7, pp. 75–84, Jan. 1995.

McCallum et al. (2000) Nat Biotechnol. 18:455–57.

Krysan et al. (1999) Plant Cell 11:2283–90.

Hofgen et al. (1994) Proc. Natl. Acad. Sci. USA 91:1726–30.

Ballinger, et al., "Targeted gene mutations in Drosophila"; *Proc. Natl. Acad. Sci. USA* vol. 86, pp. 9402–9406 (Dec. 1989).

Kaiser, et al., "'Site–selected' transposon mutagenesis of Drosophila"; *Proc. Natl. Acad. Sci. USA* vol. 87, pp. 1686–1690, (Mar. 1990).

O'Hare, et al., "Searching for needles in haystacks via the polymerase chain reaction"; *Trends in Genetics*, vol. 6, No. 7, pp. 202–203 (Jul. 1990).

Rushforth, et al., "Site–Selected Insertion of the Transposon Tc1 into a *Caenorhabkitis elegans* Myosin Light Chain Gene"; *Molecular and Cellular Biology*, pp. 902–910, (Feb. 1993).

* cited by examiner

*Primary Examiner*—John S. Brusca
*Assistant Examiner*—Marjorie A. Moran
(74) *Attorney, Agent, or Firm*—Norman J. Kruse; Christopher M. Holman

(57) ABSTRACT

The present invention provides methods of identifying a plant containing a lesion in a gene sequence flanked in a wild type chromosome by known polynucleotide sequences. The methods comprise providing a collection of nucleic acids from source plants, providing a data base that associates each nucleic acid with its source plant, amplifying the collection of nucleic acids, thereby detecting the lesion, and using the database to identify the source plant carrying the lesion.

12 Claims, No Drawings

METHOD FOR OBTAINING A PLANT WITH A GENETIC LESION IN A GENE SEQUENCE

CROSS-REFERENCES TO RELATED APPLICATIONS

This application claims the benefit of U.S. Provisional Application Ser. No. 60/080,401, filed Apr. 2, 1998, which is incorporated herein by reference in its entirety.

STATEMENT AS TO RIGHTS TO INVENTIONS MADE UNDER FEDERALLY SPONSORED RESEARCH AND DEVELOPMENT

Not applicable.

BACKGROUND OF THE INVENTION

In recent years, genomic sequencing of several organisms has been completed and genomic sequencing of many other organisms has also been initiated. Furthermore, the complete genomic sequences of many organisms, including human, some model organisms such as *C. elegans,* Drosophila and Arabidopsis, as well as some economically important crops and animals will be known within the next decade. Many of the genes identified from this research, however, will have unknown functions.

One approach to study gene functions is to knock out a gene of an organism and find out what happens to the mutant organism. Studying the mutant organism often leads to better understanding of the functions of the gene. Also, gene knockouts allow for the specifically elimination or change of undesirable traits.

Currently there are technologies available to create knock-out animals through homologous recombination. See, e.g., Galli-Taliadoros, et al. *J. Immunol. Methods* 181(1) :1–15 (1995); Buerstedde, et al., *Cell,* 67:179–88 (1991); Jasin, et al., *Genes and Devel.,* 2:1353–63 (1988); Sedivy, et al., *Proc. Natl. Acad. Sci. USA,* 86:227–31 (1989). Such technologies are expensive and inefficient. For unknown reasons, however, the frequency of homologous recombination in plants is so low that it is not possible to create a knock-out plant through homologous recombination. Although some researchers have succeeded in lowering expression levels of certain plant genes by making transgenic plants expressing antisense RNA of those genes, they can not completely eliminate the expression and function of those genes. In many cases, complete elimination of the function of a gene is needed. Also, it is currently either very difficult or impossible to make transgenic plants in many crop species.

Bensen et al. *Plant Cell* 7(1): 75–84 (1995) teach a method of identifying transposon insertion mutants in known maize gene sequences by amplifying the region between a transposon sequence and a particular gene sequence. This method, however, is limited to the few plant systems with characterized transposon systems or requires the introduction of such systems in heterologous plants. This method therefore does not provide a universal method for identification of mutations in known sequences of any plant species.

Therefore a need exists for obtaining and detecting a genetic lesion in a known plant gene sequence. Ideally, this method should be useful in as broad a range of plants as possible and therefore should not depend on such criteria as availability of transformation methods.

SUMMARY OF THE INVENTION

The present invention provides a method for identifying a plant containing a lesion in a gene sequence. The method comprises providing a collection or pool of nucleic acid samples wherein each sample is collected from an individual plant. Typically the individual plants used in the method are derived from a mutagenized population of source plants, thereby insuring genetic diversity within the population.

The method of the invention also provides a database that associates each nucleic acid sample with the source plant from which the nucleic acid sample was derived.

In addition, the method of the invention includes amplifying the collection of nucleic acids using primers that specifically hybridize to known polynucleotide sequences that flank the gene sequence in the wild type chromosome. In one embodiment, the amplification includes an extension step that is shortened to selectively amplify a nucleic acid with the lesion. For instance, the extension time can be between 0.5 and two minutes at 72° C. In one embodiment, the extension time is 1.5 minutes.

After the nucleic acids are amplified, a genetic lesion within the gene sequence of one of the samples is detected. For instance, the lesion can be detected as a change in size of the amplification product. Once the nucleic acid sample containing the lesion is identified, the database is used to identify the source plant from which the nucleic acid sample was derived.

In one embodiment, the lesion is a deletion.

In another embodiment, the collection of nucleic acids is divided into subset pools before the lesion is detected. For example, the pools can contain nucleic acids from about 100 different to about 3000 different source plants. In another embodiment, the pools can contain at least about 1500 different source plants.

The plurality of source plants or the progenitors of the source plants can, for example, be contacted with a mutagen. In one embodiment, the mutagen is fast neutrons.

In one embodiment, the distance between the known nucleotide sequences in the wild type plant is between about three kilobases and seven kilobases.

The method of the invention can be performed, for instance, on a plurality of source plants such as rice, tomato or Arabidopsis. In one embodiment, the number of source plants is about 10,000 to about 50,000.

Included in the invention is a plant identified by the method described above.

In a preferred embodiment of the invention, a source plant carrying a deletion in a gene sequence is identified. In this embodiment, a collection of nucleic acids from a plurality of mutagenized plants, at least one of which carries a deletion in the gene sequence, is provided. A database is also provided that associates each nucleic acid in the collection with the nucleic acid's source plant. The collection of nucleic acids is then amplified. The amplification comprises providing primers that specifically hybridize to polynucleotide sequences from about 3 kb to about 7 kb apart in the wild type chromosome and that specifically hybridize to polynucleotide sequences within or flanking the gene sequences. The amplification further comprises an extension step of between about 0.5 minutes to about two minutes at 72° C., thereby preferentially amplifying the nucleic acids with the deletion. The presence of the nucleic acid with the deletion is confirmed by comparing the amplification product with an amplification product from a wild type plant. The database is then used to identify the source plant with the deletion, thereby providing a plant with a deletion in the gene sequence for evaluation of a mutant phenotype associated with the deletion.

Definitions

A "gene sequence" refers to a nucleic acid sequence that comprises a sequence or subsequence from an open reading frame and/or regulatory sequences in genomic DNA or a cDNA.

A "wild type chromosome" refers to a polynucleotide sequence that exists in a plant before human-initiated mutagenesis is performed. "Human initiated mutagenesis" does not include, for instance, selection of agronomically valuable traits through selective breeding, but does include the introduction of mutagenic compounds or elements to promote genetic diversity in a population. Such mutagenic compounds include, e.g., transposons.

A "source plant" is a particular plant from which nucleic acids were harvested or the plant's genetic equivalent. For the purposes of this invention, genetically equivalent plants are those plants from which the same specific genetic lesion can be recovered. Genetically equivalent plants includes siblings or progeny from a plant of interest. Thus, if M1 seeds are mutagenized, grown into M1 plants and their M2 seed are harvested, pooled M2 seeds from the same parent are the same "source plant" because a specific mutation of one M2 plant that was received from an M1 parent is likely to be found in a pool of M2 siblings from the same M1 parent. Similarly, if an M2 plant has a particular genetic lesion, pools of M3 progeny from the M2 plant will also likely carry that lesion.

A "lesion" can be any molecular alteration of a nucleic acid relative to wild type plant nucleic acids. For instance, a lesion can be a deletion, inversion, insertion, duplication or a rearrangement in a nucleic acid sequence. The lesion is preferably deletion.

"Progenitors of the plurality of source plants" are the ancestors of a particular collection of source plants. For instance, if M1 seed is mutagenized, grown into M1 plants and then M2 seed is collected from the M1 plants, the M1 plants are progenitors of the M2 plants.

"Evaluation of a mutant phenotype" refers to identifying physical traits of a plant carrying a genetic lesion that differ from the traits of a wild type plant. The manifestation of such traits can be dependent on the genetic makeup of the plant, e.g. whether the plant is homozygous or heterozygous for a particular allele, including the allele containing the lesion, as well as the overall genetic background. If the lesion causes a homozygous lethal phenotype then the lesion can be maintained in future generations in the heterozygous state The phrase "nucleic acid sequence" refers to a single or double-stranded polymer of deoxyribonucleotide or ribonucleotide bases read from the 5' to the 3' end. It includes chromosomal DNA, self-replicating plasmids, infectious polymers of DNA or RNA and DNA or RNA that performs a primarily structural role.

The term "promoter" refers to regions or sequence located upstream and/or downstream from the start of transcription and which are involved in recognition and binding of RNA polymerase and other proteins to initiate transcription. A "plant promoter" is a promoter capable of initiating transcription in plant cells.

The term "plant" includes whole plants, shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety).

"Recombinant" refers to a human manipulated polynucleotide or a copy or complement of a human manipulated polynucleotide. For instance, a recombinant expression cassette comprising a promoter operably linked to a second polynucleotide may include a promoter that is heterologous to the second polynucleotide as the result of human manipulation (e.g., by methods described in Sambrook et al., *Molecular Cloning—A Laboratory Manual,* Cold Spring Harbor Laboratory, Cold Spring Harbor, N.Y., (1989) or Current Protocols in Molecular Biology Volumes 1–3, John Wiley & Sons, Inc. (1994–1998)) of an isolated nucleic acid comprising the expression cassette. In another example, a recombinant expression cassette may comprise polynucleotides combined in such a way that the polynucleotides are extremely unlikely to be found in nature. For instance, human manipulated restriction sites or plasmid vector sequences may flank or separate the promoter from the second polynucleotide. One of skill will recognize that polynucleotides can be manipulated in many ways and are not limited to the examples above.

A polynucleotide "exogenous to" an individual plant is a polynucleotide which is introduced into the plant by any means other than by a sexual cross. Examples of means by which this can be accomplished are described below, and include Agrobacterium-mediated transformation, biolistic methods, electroporation, and the like. Such a plant containing the exogenous nucleic acid is referred to here as a $T_1$ (e.g. in Arabidopsis by vacuum infiltration) or $R_0$ (for plants regenerated from transformed cells in vitro) generation transgenic plant. Transgenic plants that arise from sexual cross or by selfing are descendants of such a plant.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule.

Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11–17 (1988) e.g., as implemented in the program PC/GENE (Intelligenetics, Mountain View, Calif., USA).

The phrase "substantially identical," in the context of two nucleic acids or polypeptides, refers to sequences or subsequences that have at least 60%, preferably 80%, most preferably 90–95% nucleotide or amino acid residue identity when aligned for maximum correspondence over a comparison window as measured using one of the following sequence comparison algorithms or by manual alignment and visual inspection. This definition also refers to the complement of a test sequence, which has substantial sequence or subsequence complementarity when the test sequence has substantial identity to a reference sequence.

One of skill in the art will recognize that two polypeptides can also be "substantially identical" if the two polypeptides are immunologically similar. Thus, overall protein structure may be similar while the primary structure of the two polypeptides display significant variation. Therefore a method to measure whether two polypeptides are substantially identical involves measuring the binding of monoclonal or polyclonal antibodies to each polypeptide. Two polypeptides are substantially identical if the antibodies specific for a first polypeptide bind to a second polypeptide with an affinity of at least one third of the affinity for the first polypeptide.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra) These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). (see, e.g., Creighton, Proteins (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes,* "Overview of principles of hybridization and the strategy of nucleic acid assays" (1993). Generally, highly stringent conditions are selected to be about 5–10° C. lower than the thermal melting point ($T_m$) for the specific sequence at a defined ionic strength pH. Low stringency conditions are generally selected to be about 15–30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 time background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions.

In the present invention, genomic DNA or cDNA comprising ANT nucleic acids of the invention can be identified in standard Southern blots under stringent conditions using the nucleic acid sequences disclosed here. For the purposes of this disclosure, suitable stringent conditions for such hybridizations are those which include a hybridization in a buffer of 40% formamide, 1 M NaCl, 1% SDS at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cased, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., an RNA gel or DNA gel blot hybridization analysis.

DESCRIPTION OF THE SPECIFIC EMBODIMENTS

The present invention provides, for the first time, a method for determining the function of a gene sequence by screening for a genetic lesion in the gene sequence. The method involves identifying plants carrying the genetic lesion by amplifying a polynucleotide sequence comprising the gene sequence from a large number of plants and then comparing the amplification products with an amplification product from wild type plants. In preferred embodiments, a nucleic acids from a plurality of source plants are pooled and amplified. In a preferred embodiment, amplification conditions are provided such that nucleic acids with a genetic lesion in a particular gene sequence is preferentially amplified.

Plant Sources of the Invention

The present invention can be used with any species of plant. The invention has use over a broad range of plants, including species from the genera Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoseyamus, Lactuca, Linum, Lolium, Lupinus, Lycopersicon, Malus, Manihot, Majorana, Medicago, Nicotiana, Olea, Oryza, Panieum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna, and Zea. In preferred embodiments, Oryza (rice), Lycopersicon (tomato) or Arabidopsis are used.

The present invention provides a collection of nucleic acids from a plurality of plants. The plurality of plants can be any collection of plants that carry genetic variation. In a preferred embodiment of the invention, the plurality of plants or the progenitors of the plants have been exposed to a mutagen likely to cause genetic lesions, thereby promoting genetic variation within the population. The mutagen is preferably chosen so as to produce a high percentage of deletions.

Plant mutatgenesis

A mutagenized population of seeds can be obtained or created. For instance, an existing mutagenized population of plants can be ordered or obtained from commercial or non-commercial suppliers (see, e.g., Lehle Seed, Round Rock, Texas and the Arabidopsis Biological Resource Center for mutagenized Arabidopsis seeds). Alternatively, a mutagenized population can be developed for any plant species. For instance, seeds or other plant material can be treated with a mutagenic chemical substance, according to standard techniques. Such chemical substances include, but are not limited to, the following: diepoxybutane, diethyl sulfate, ethylene imine, ethyl methanesulfonate and N-nitroso-N-ethylurea. Alternatively, ionizing radiation from sources such as, for example, X-rays, gamma rays or fast neutron bombardment can be used.

A mutagenized population is typically developed by generating a large number of seed (~50,000) and exposing the seed to a mutagen. One of skill will recognize that a series of concentrations and time of exposures is used to determine the proper level of mutagenesis. Typically such test populations are planted in soil or plated onto solid growth media. The number of seed that do not germinate is a good indicator of the extent of mutagenesis. Preferably the mutagenized population will typically have a high enough frequency of mutation to identify the desired mutation in as small a number of plants possible, while avoiding overmutagenizing the population such that a typical plant carries multiple different genetic lesions and to ensure that most plants grown from the mutagenized seeds will produce seeds for the next generation. Theoretically, an ideal dose will be the one that makes about 37% of plants grown from the treated seeds sterile.

In one embodiment, seed (designated M1) are mutagenized, grown into plants, and M2 seed is harvested from them. Plant populations with plants that are homozygous and heterozygous for genetic lesions (e.g., M2 populations) are preferably used as the nucleic acid source for the present invention. Typically M2 plants are grown and leaf or root tissue is harvested for nucleic acid isolation. M3 seed can be collected from the M2 plant, thereby producing a source plant population that can be later used to recover any genetic lesion in the parent M2 plant. Alternatively, the siblings (as seed or plants) of the M2 plant are saved to provide a source plant population. This second embodiment saves plant growing space but adds an additional step later to recover a desired genetic lesion.

Type of genetic lesions

Mutagens can produce, inter alia, point mutations, deletions, inversions, insertions, duplications and rearrangements. Genetic lesions can be large or small. For the present invention, a preferred lesion significantly changes the distance between the primers that hybridize to the two known polynucleotide sequences. Such lesions include deletions, insertions and duplications. A significant change is one that can be readily detected using standard procedures for specifically detecting nucleic acids, e.g., PCR. Typically a change of greater than at least 30% of the distance between the primers that hybridize to the two known polynucleotides is preferred. In an especially preferred embodiment, the genetic lesion is a deletion that removes from at least about 10% to about 85% of the distance between the primers. For instance, in a typical case, the primers are selected to be about 7 kb apart and the deletion is about 0.5 kb to about 6 kb.

Preparation of nucleic acids from the plurality of plants

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual,* Cold Spring Harbor Laboratory, Cold Spring Harbor, N.Y., (1989) or Current Protocols in Molecular Biology Volumes 1–3, John Wiley & Sons, Inc. (1994–1998).

Databases of the Invention

In preferred embodiments of the present invention, nucleic acids are isolated from individual plants and then subsequently pooled to perform the method of the invention. A unique number or code is provided for nucleic acid preparations from each individual plant and the same name or code is used to track and maintain each source plant population.

In one embodiment, the assays of this invention are facilitated by the use of databases to record assay results. Particularly with the use of large-scale screening systems, (e.g., screening large populations of planta )data management can be extremely useful. Maintenance and management of the information obtained by screening such a library is aided by methods automated information retrieval, e.g. a computer database.

Such a database is useful for a variety of functions, including, but not limited to library registration, library or result display, library and/or result specification, documentation, and data retrieval and exploratory data analysis. The registration function of a database provides recordation/registration of plant and nucleic acid sources. Library and screening result display functions provide an effective means to review and/or categorize relevant assay data. The database also can provide documentation of screening results and the ability to rapidly retrieve, correlate (or statistical analysis), and evaluate assay data.

The database can be any medium convenient for recording and retrieving information generated by the assays of this invention. Such databases include, but are not limited to manual recordation and indexing systems (e.g. file-card indexing systems). However, the databases are most useful when the data therein can be easily and rapidly retrieved and manipulated (e.g. sorted, classified, analyzed, and/or otherwise organized). Thus, in a preferred embodiment, the signature the databases of this invention are most preferably "automated", e.g., electronic (e.g. computer-based) databases. The database can be present on an individual "stand-alone" computer system, or a component of or distributed across multiple "nodes" (processors) on a distributed computer systems. Computer systems for use in storage and manipulation of databases are well known to those of skill in the art and include, but are not limited to "personal computer systems", mainframe systems, distributed nodes on an inter- or intra-net, data or databases stored in specialized hardware (e.g. in microchips), and the like.

Amplification

The invention provides for an amplification step to generate an appropriate amount of nucleic acids to resolve difference in a particular sequence between a nucleic acid carrying a lesion and a wild type nucleic acid.

PCR

In a preferred embodiment, the polymerase chain reaction (PCR) is used to amplify both wild type and mutant DNA within a pooled sample. PCR, as described in U.S. Pat. Nos. 4,683,195 and 4,683,202 to Mullis and Mullis et al., describe a method for increasing the concentration of a segment of target sequence in a mixture of genomic DNA without cloning or purification. PCR can be used to directly increase the concentration of the target to an easily detectable level. The process for amplifying the target sequence involves introducing a molar excess of two oligonucleotide primers that are complementary to their respective strands of the double-stranded target sequence to the DNA mixture containing the desired target sequence. The mixture is denatured and then allowed to hybridize. Following hybridization, the primers are extended with polymerase so as to form complementary strands. The steps of denaturation, hybridization, and polymerase extension can be repeated as often as needed, in order to obtain relatively high concentrations of a segment of the desired target sequence. For a general overview of PCR see PCR Protocols: *A Guide to Methods and Applications.* (Innis, M, Gelfand, D., Sninsky, J. and White, T., eds.), *Academic Press,* San Diego (1990).

The length of the segment of the desired target sequence is determined by the relative positions of the primers with respect to each other, as well as the length of time that the polymerase is allowed to extend the DNA strand ("the extension time"). Therefore, this length is a controllable parameter.

In a preferred embodiment of the present invention, an extension time is chosen such that nucleic acids containing the genetic lesion are preferentially amplified. For instance, if the genetic lesion is suspected to be a deletion, a shorter extension time is used so that proper amplification only occurs if the distance between the primers is less than is found in a wild type plant. One of skill can design amplification conditions based on the expected deletion size, distance between the primers, and the like. For example, in some embodiments, the extension time can be from about one minute to about two minutes at 72° C. In a more preferred embodiment, the extension time is 1.5 minutes at 72° C.

Designing primers

Primers appropriate for the invention will depend upon the gene sequence of interest. Primer construction and use are well known to those of skill in the art. In preferred embodiments, the primers are constructed to hybridize to polynucleotides that flank the gene sequence. The polynucleotide sequences can flank the coding region of the gene of interest or they can flank the coding sequence and regulatory sequences (e.g., promoter and 3' regions of the gene). Alternatively, the primers can be constructed to hybridize within the regulatory or coding regions of the gene. It is preferred that the primers hybridize to polynucleotides from about 3 kb to about 7 kb apart.

In species where extensive DNA sequencing has been performed, such as Arabidopsis, it is likely that genomic sequences flanking a gene sequence of interest will be known. If so, primer sequences can be developed from existing known genomic sequences. If the genomic sequences flanking a gene sequence of interest are not available, known polynucleotide sequences that flank the gene sequence of interest can be developed. For instance, genomic libraries (cosmid, BAC, YAC, etc.) can be screened for clones that contain the gene of interest and the ends of the inserts in such clones can be sequenced. Alternatively, restriction enzyme mapping of a particular genomic region can be performed, followed by nucleotide sequencing of the region flanking the gene of interest. Primers can then be derived from such sequences.

Long Range PCR

In one embodiment of the invention, the collection of nucleic acids are amplified using long range PCR (see, e.g., 5. Page 17, line 13, *Proc. Natl. Acad. Sci. U.S.A.* 9: 2216–2220, (1994); Blood, 88(3): 985–994 (1996)) Recently several thermostable DNA polymerases that can amplify DNA fragments up to 35 kb have become available commercially. By designing primer pairs separated by a long distance of up to 35 kb, a significantly larger region can be amplified.

To analyze such large nucleic acids, the amplified DNA fragment is then digested by a restriction enzyme and analyzed by gel electrophoresis. The DNA can be detected by staining the gel with ethidium bromide or fluorescent dye. Preferably, DNA deletions or rearrangements within the region will create additional DNA fragment(s) compared to wild type. Long range PCR is also useful to detect large deletion around a gene.

Other amplification methods

The desired nucleic acids can also be identified using other well known amplification techniques. Examples of protocols sufficient to direct persons of skill through in vitro amplification methods, including the ligase chain reaction (LCR), Qβ-replicase amplification and other RNA polymerase mediated techniques are found in Berger, Sambrook, and Ausubel, as well as Arnheim & Levinson (Oct. 1, 1990) *C&EN* 36–47; *The Journal Of NIH Research* (1991) 3: 81–94; (Kwoh et al. (1989) *Proc. Natl. Acad. Sci. USA* 86: 1173; Guatelli et al. (1990) *Proc. Natl. Acad. Sci. USA* 87: 1874; Lomell et al. (1989) *J. Clin. Chem.* 35: 1826; Landegren et al. (1988) *Science* 241: 1077–1080; Van Brunt (1990) *Biotechnology* 8: 291–294; Wu and Wallace (1989) *Gene* 4: 560; and Barringer et al. (1990) *Gene* 89: 117.

Improved methods of cloning in vitro amplified nucleic acids are described in Wallace et al., U.S. Pat. No. 5,426, 039.

Analysis of amplification products

Analysis of the amplification products comprises comparing the amplification products from a sample (e.g. a plant containing a genetic lesion or products from a pool of plants, one or more of which contain the lesion) to a similar amplification product of a wild type plant. Preferably the amplification products are separated based on their length. Alterations in the size of the sample amplification product compared to the wild type product indicates that a nucleic acid with a genetic lesion at the gene sequence of interest is in the sample. For instance, amplification of a smaller DNA fragment from the sample than from the wild type indicates that at least one individual plant from the sample has a deletion within the gene sequence of interest. This result can be confirmed and if the sample is a pool of nucleic acids, then subpools or individual members of the pool can be individually amplified to identify the nucleic acid carrying the lesion. Once the nucleic acid is identified, the database can be used to identify the source plant associated with the nucleic acid.

The amplification products can be analyzed by a number of techniques, including electrophoresis and hybridization. Preferably the amplification products are analyzed using electrophoresis and ethidium bromide staining (see, e.g., Sambrook, et al.), followed by visual inspection.

Alternatively, to increase the detection limit of the amount of DNA fragments on the gel, the DNA fragments can be transferred to a membrane by southern blotting and hybridized with radioactive or nonradioactive probes specific to the target gene. After hybridization, very small amount of DNA (<1 pg) can be detected by autoradiography or other detection methods. Because of this great sensitivity, a large number of DNA samples can be pooled together as one sample and checked for deletion mutation(s). This embodiment is particularly helpful if it is difficult to resolve the amplification products clearly using ethidium bromide followed by visual inspection.

Hybridization

An alternative method of resolving differences between wild type and pools carrying mutant alleles of a gene involves hybridization. In this embodiment, pools of nucleic acids from mutagenized plants are digested with restriction enzymes and the resulting nucleic acid fragments are separated by electrophoresis and blotted (e.g. Southern blotting). See, e.g., Sambrook et al. The resulting blots are subsequently probed with a probe of the gene of interest and compared to similar samples of wild type nucleic acids. Hybridization of the probe in the pooled sample to nucleic acid fragments of different size than wild type indicates a genetic lesion exists in the pool. The method can then be repeated with individual members of the pool to determine which individual carries the lesion. As described above, once the nucleic acid is identified, the database can be used to identify the source plant associated with the nucleic acid.

Determination of a Mutant Phenotype

The particular endogenous sequence targeted in the methods of the invention is not a critical aspect of the invention. Examples of genes that can be targeted using the present invention include genes conferring resistance to pathogens (for example, insects, fungi, bacteria and viruses), storage protein genes, herbicide resistance genes, and genes involved in biosynthetic pathways, such as oil production. Other examples include Cytochrome P450 and related enzymes, transcription factors, genes that are essential for plant growth and development, and homologs of genes with known function.

Plants identified by the methods of the invention (e.g., mutants) may have useful phenotypes themselves. For instance, mutations in certain biosynthetic pathways can lead to a useful alteration of a plant's metabolism. Alternatively, once the phenotype of a mutant is known, ectopic or heterologous expression of the wild type gene can be hypothesized and tested. In particular, appropriate genetic backgrounds can be identified to alter plant phenotypes. For example, the phenotypic expression of a particular transgene may be concealed by a wild type homolog or ortholog. Once a mutant allele's phenotype is determined, it is possible to identify genetic backgrounds where such effect is limited.

The following example is offered by way of illustration, not limitation.

EXAMPLE 1

This example shows that a plant carrying a genetic lesion in a gene sequence can be identified within a pooled sample. To simulate screening a pooled population of mutagenized plants for a deletion in s specific gene, small amounts of DNA from Arabidopsis plants carrying the gal-3 allele of GA1 (Plant Cell 4:119–128 (1992)) was mixed with wild type DNA and then amplified. The gal-3 allele contains a 5 kb deletion relative to wild type GA1. Primers that hybridize to polynucleotide sequences that are about 6.4 kb apart in wild type Arabidopsis and that flank the 5 kb deletion in gal-3 were used. The 5' primer was: cggagaagcttcttctggagtcagag. The 3' primer was: gcaaacttgatctaccatatgtcatc.

Two micrograms of wild type Arabidopsis DNA was mixed with 1 ng, 2.5 ng, 5 ng and 10 ng of gal-3 DNA in a 25 µl PCR reaction including 1.5 U of Taq polymerase. The samples were amplified using the following conditions. The reaction was incubated at 94 C. for 2 min followed by 40 cycles of 94° C., 30 seconds; 65° C., 30 seconds; and 72° C., 1.5 minutes. The cycles were followed by a final step of 72° C., for 7 minutes.

The resulting products were analyzed using electrophoresis and then visualized using ethidium bromide. At every dilution the smaller, 1.4 kb product from gal-3 was clearly detectable, in addition to the wild type 6.4 kb DNA fragment. These results indicate that one deletion in at least about 2000 wild type plants can be detected. Thus using the methods of the invention, pools of up to at least 2000 individual plants can be screened to successfully identify a single individual carrying a lesion in a particular gene sequence of interest.

The above example is provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

What is claimed is:

1. A method of identifying a plant containing a deletion in a gene sequence, the method comprising:

(a) providing a collection of nucleic acids derived from a plurality of source plants, wherein the nucleic acids comprise the gene sequence, or the gene sequence with a deletion, and at least one of the nucleic acids comprises the gene sequence with a deletion, and wherein the gene sequence or gene sequence with the deletion is flanked by a 5' flanking polynucleotide sequence and 3' flanking polynucleotide sequence;

(b) providing a database that associates each nucleic acid in the collection with the source plant from which the nucleic acid was derived;

(c) amplifying the gene sequence with the deletion from the collection of nucleic acids using a first primer that specifically hybridizes to the 5' flanking polynucleotide sequence, or its complement, and a second primer that specifically hybridizes to the 3' flanking polynucleotide sequence, or its complement, wherein the amplification includes a shortened extension step, the length of which is chosen so that proper amplification only occurs if the distance between the primers is less than is the case when the gene sequence lacks a deletion, whereby the gene sequence with the deletion is preferentially amplified compared to the gene sequence lacking a deletion;

(d) detecting the preferential amplification of the gene sequence with the deletion compared to the amplification of the gene sequence lacking a deletion, thereby identifying a nucleic acid comprising the gene sequence with a deletion; and (e) identifying the source plant from which the nucleic acid identified in step (d) was derived by referring to the database provided in step (b), thereby identifying a plant containing a deletion in the gene sequence.

2. The method of claim 1, wherein the amplification step includes an extension time that results in preferential amplification of the gene sequence with the deletion compared to amplification of the gene sequence lacking a deletion.

3. The method of claim 2, wherein the extension time is between about 0.5 to about 2 minutes at about 72° C.

4. The method of claim 3, wherein the extension time is about 1.5 minutes at 72° C.

5. The method of claim 1, wherein the collection of nucleic acids is combined into pools before the amplification step.

6. The method of claim 5, wherein each pool contains nucleic acids from about 100 different source plants to about 3000 different source plants.

7. The method of claim 5, wherein each pool contains nucleic acids from at least 1500 different source plants.

8. The method of claim 1, wherein the plurality of source plants or progenitors of the plurality of source plants were contacted with a mutagen that causes deletion mutations.

9. The method of claim 8, wherein the mutagen is fast neutrons.

10. The method of claim 1, wherein the distance between the 5' flanking polynucleotide sequence and the 3' flanking polynucleotide sequence when there is no deletion in the gene sequence is between about 3 kilobases to about 7 kilobases.

11. The method of claim 1, wherein the plurality of source plants is selected from rice, tomato and Arabidopsis.

12. The method of claim 1, wherein the plurality of source plants comprises about 10,000 to about 50,000 source plants.

* * * * *